United States Patent
Sander

(10) Patent No.: US 11,458,159 B2
(45) Date of Patent: Oct. 4, 2022

(54) OXYGEN CARRIERS FOR THE TREATMENT OF SKIN INDISPOSITIONS

(71) Applicant: Mölnlycke Health Care AB, Gothenburg (SE)

(72) Inventor: Michael Sander, Bielefeld (DE)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 244 days.

(21) Appl. No.: 16/625,566

(22) PCT Filed: Jun. 20, 2018

(86) PCT No.: PCT/EP2018/066447
§ 371 (c)(1),
(2) Date: Dec. 20, 2019

(87) PCT Pub. No.: WO2019/002051
PCT Pub. Date: Jan. 3, 2019

(65) Prior Publication Data
US 2021/0401875 A1 Dec. 30, 2021

(30) Foreign Application Priority Data
Jun. 26, 2017 (EP) .................................. 17177946

(51) Int. Cl.
*A61K 33/00* (2006.01)
*A61K 38/42* (2006.01)

(52) U.S. Cl.
CPC .............. *A61K 33/00* (2013.01); *A61K 38/42* (2013.01)

(58) Field of Classification Search
CPC ................. A61K 33/00; A61K 38/42
See application file for complete search history.

(56) References Cited

U.S. PATENT DOCUMENTS

| 5,686,102 A | * | 11/1997 | Gross ..................... A61Q 19/00 424/450 |
| 11,116,868 B2 | * | 9/2021 | Sander ................ A61L 26/0066 |
| 2003/0180365 A1 | | 9/2003 | Barnikol |
| 2010/0063004 A1 | * | 3/2010 | Chaudhuri ............... A61K 9/06 514/86 |
| 2014/0221944 A1 | * | 8/2014 | Sander .................... A61P 17/02 604/310 |

FOREIGN PATENT DOCUMENTS

| EP | 2550973 | 1/2013 |
| EP | 2614833 | 7/2013 |
| WO | 03082392 | 10/2003 |

OTHER PUBLICATIONS

MayoClinic Bedsores (pressure ulcers) ([online] retrieved on Feb. 17, 2022 from: https://www.mayoclinic.org/diseases-conditions/bed-sores/symptoms-causes/syc-20355893?p=1; 5 pages) (Year: 2022).*
Larry Jeffus Metal Fabrication Technology for Agriculture 2010 pp. 16-17. (Year: 2010).*
Hunt et al., "Clinical effectiveness of hemoglobin spray (Granulox) as adjunctive therapy in the treatment of chronic diabetic foot ulcers", Diabetic Foot & Ankle, vol. 7, No. 1, Jan. 8, 2016, 9 pages.
PCT/EP2018/066447, "International Search Report and Written Opinion", dated Aug. 30, 2018, 10 pages.
Scottish Health Technologies Group, "Granulox haemoglobin spray", retrieved from the internet: at http://granulox.de/downloads/Scottland-Granulox-Review-v1.0.pdf, Jan. 1, 2016, 6 pages.

* cited by examiner

*Primary Examiner* — Ernst V Arnold
(74) *Attorney, Agent, or Firm* — Kilpatrick Townsend & Stockton LLP

(57) ABSTRACT

The present invention refers to an oxygen carrier, preferably hemoglobin or myoglobin, for use in the treatment of an unpleasant feeling of a body surface due to a disease or a disorder.

12 Claims, No Drawings

OXYGEN CARRIERS FOR THE TREATMENT OF SKIN INDISPOSITIONS

CROSS-REFERENCE TO RELATED APPLICATIONS

The present application is a U.S. national phase application under 35 U.S.C. § 371 of PCT/EP2018/066447, filed on Jun. 20, 2018, which claims the benefit of priority to EP Application No. 17177946.5, filed on Jun. 26, 2017, the entire contents of each of which are incorporated by reference herein for all purposes.

The present invention refers to oxygen carriers like hemoglobin or a hemoglobin comprising composition for the treatment of sites on a body surface developing an unpleasant feeling due to a acquired or self-established disorder. In particular, the invention refers to the treatment of body sites developing an unpleasant feeling due to either the infection by any virus species or by a body condition effecting any indisposition, like e.g. itching, stinging or pain, with the oxygen carrier or oxygen carrier comprising composition for reducing said unpleasing, aggravating or even painful feeling.

Several disorders of the body results in an unpleasant feeling of the body surface, e.g. itching, stinging or pain of body sites, wherein the disorder either is acquired, e.g. by infection of the body, or is an immunological (dys)regulation of the immune system. Examples of infectious diseases resulting in painful reactions of the body surfaces are infections with viruses.

Herpesviridae is a large family of DNA viruses that cause diseases in animals, including humans. The members of this family are also known as herpes viruses. The family name is derived from the Greek word herpein ("to creep"), referring to the latent, recurring infections typical of this group of viruses. Herpesviridae can cause latent or lytic infections.

At least five species of Herpesviridae—HSV-1 and HSV-2 (both of which can cause orolabial herpes and genital herpes), varicella zoster virus (the cause of chickenpox and shingles), Epstein-Barr virus (implicated in several diseases, including mononucleosis and some cancers), and cytomegalovirus—are extremely widespread among humans. More than 90% of adults have been infected with at least one of these, and a latent form of the virus remains in most people.

There are 9 herpesvirus types known to infect humans: herpes simplex viruses 1 and 2, HSV-1 and HSV-2, (also known as HHV1 and HHV2), varicella-zoster virus (VZV, which may also be called by its ICTV name, HHV-3), Epstein-Barr virus (EBV or HHV-4), human cytomegalovirus (HCMV or HHV-5), human herpesvirus 6A and 6B (HHV-6A and HHV-6B), human herpesvirus 7 (HHV-7), and Kaposi's sarcoma-associated herpesvirus (KSHV, also known as HHV-8). In total, there are more than 130 known herpesviruses, some of them from mammals, birds, fish, reptiles, amphibians, and mollusks.

Chickenpox, also known as varicella, is a highly contagious disease caused by the initial infection with varicella zoster virus (VZV). The disease results in a characteristic skin rash that forms small, itchy blisters, which eventually scab over. It usually starts on the chest, back, and face then spreads to the rest of the body. An affected person tends to scratch the itching body areas which further supports the unpleasant feeling up to pain. Other symptoms may include fever, feeling tired, and headaches. Symptoms usually last five to ten days.https://en.wikipedia.org/wiki/Chickenpox—cite_note-CDC2011SS-1 The disease is often more severe in adults than children. Symptoms begin ten to twenty-one days after exposure to the virus. After a chickenpox infection, the virus remains dormant in the body's nerve tissues. The immune system keeps the virus at bay, but later in life, usually in an adult, it can be reactivated and cause a different form of the viral infection called shingles (also known as herpes zoster).

Pain can be described as an unpleasant feeling of the body putting great strain to a person. One type of pain is neuropathic pain, caused by a damage or disease affecting the somatosensory nervous system. Neuropathic pain may be associated with abnormal sensations called dysesthesia or pain from normally non-painful stimuli (allodynia). It may have continuous and/or episodic (paroxysmal) components. Common qualities include burning or coldness, "pins and needles" sensations, numbness and itching, without being restricted to these.

Common causes of painful peripheral neuropathies are viral infections, (in particular infections with herpes viruses, e.g. herpes zoster infection), HIV-related neuropathies, nutritional deficiencies, toxins, remote manifestations of malignancies, immune mediated disorders and physical trauma to a nerve trunk.

Such painful conditions commonly are treated with analgetic compounds, applied systemically (typically either orally or intraveneously). A topical treatment of painful conditions sometimes is carried out with anti-inflammatory or as well with analgetic compounds.

In modern therapy concepts there exist a desire to treat unpleasant conditions of a living body with effective, but less "harmful", but more "natural" compounds. Therefore it was the object of the present invention to provide a compound and composition for alleviating unpleasant feelings on a surface of a living body caused by a disorder or disease of said body, wherein said compound or composition is effective, whilst being similar to naturally occurring compounds and can be applied to said body site preferably topically.

This object is met by the compound and composition as defined in the claims.

The compound used according to the present invention to alleviate the unpleasant feeling of pain, itching, stinging, burning or similar is an oxygen carrier, allowing to provide oxygen to the affected body site or area. Preferably, said oxygen carrier is a hemoglobin or a myoglobin—compounds naturally occurring in blood—wherein said compound is stabilized by charging on its oxygen-binding site with a non-O2 ligand during preparation and storing.

During the preparation and storage of oxygen carriers on basis of hemoglobin or myoglobin they can lose their functionality partially or completely. To prevent this it is desirable to stabilize the oxygen carriers that they remain usable and able to transport oxygen.

Generally, there are different approaches to the preparation of oxygen carriers; one of them is the preparation of suitable solutions of native or chemically modified hemoglobins (see "Issues from Vth International Symposium on Blood Substitutes, San Diego, Calif., USA, March 1993", Artificial Cells, Blood Substitutes, and Immobilization Biotechnology 22 (1994), vol. 2-vol. 4). One problem in the handling of such pharmaceutical preparations as artificial oxygen carriers is their increasing inactivation by spontaneous oxidation to methemoglobin which is no longer able to transport oxygen. This occurs usually during preparation by the producer and the subsequent storage.

Several approaches for solving this problem are described. Either it is tried to minimize the degree of oxidation of hemoglobin, or to reduce the oxidized hemoglobin back again.

One possibility for prevention of spontaneous oxidation is deoxygenating the hemoglobin (i.e., entirely removing oxygen from the preparation), since desoxyhemoglobin oxidizes much more slowly to methemoglobin than oxyhemoglobin.

Further it is possible to minimize the amount of oxidation by storage and/or preparation at the lowest possible temperature (for aqueous solutions, at about 4° C.).

EP 0 857 733 describes that hemoglobin may be stabilized by binding a ligand, in particular carbon monoxide, to the oxygen binding site. It was found that such a carbonylhemoglobin can be applied to an organism without de-ligandation and is suitable as an oxygen carrier inside of the blood stream.

According to the invention a natural (native) oxygen carrier, particularly hemoglobin or myoglobin or a modified derivative thereof, or mixtures thereof, is/are used. Hemoglobin or myoglobin of human or animal origin, in particular of equine, bovine or preferably porcine origin, is particularly suitable for the present invention. Human or porcine hemoglobin, which is natural or modified as described below, is particularly preferred as an oxygen carrier. The oxygen carrier may be freshly isolated from human or animal blood or may be artificially prepared.

Mixtures of natural and modified oxygen carrier can also be used, such as, for example, in a ratio of 20:1 to 1:20, with reference to weight. Further, mixtures of hemoglobin and myoglobin, or their modified derivatives may be used in the aforementioned ratio of 20:1 to 1:20.

In a further embodiment the oxygen carrier may be modified. The modification can be an intramolecular cross-linking, polymerization (intermolecular cross-linking), pegylation (covalent linking with polyalkylene oxides), modification with chemically reactive effectors such as pyridoxal-5'-phosphate or 2-nor-2-formyl-pyridoxal-5'-phosphate, or also with chemically non-reactive effectors of the oxygen bond, such as 2,3-bisphosphoglycerate, inositol hexaphosphate, inositol hexasulfate, or mellitic acid, or a combination thereof. Such modifications are known and described, for example, in DE-A 100 31 744, DE-A 100 31 742, and DE-A 100 31 740. Cross-linking of oxygen carriers is also described in DE 197 01 37, EP 97 1000790, DE 44 18 937, DE 38 41 105, DE 37 14 351, DE 35 76 651.

Examples for modified oxygen carriers are hemoglobins having a molecular weight of 65,000 to 15,000,000, such as intramolecularly cross-linked molecules according to WO 97/15313, particularly polymer products as well as intermolecularly cross-linked products having an average molecular weight of 80,000 to 10,000,000 g/mol, particularly 100,000 to 5,000,000, or analogously produced myoglobins having a molecular weight of 16,000 to 5,000,000, particularly 100,000 to 3,000,000, preferably 1,000,000 g/mol. Those oxygen carriers that are polymerized, for example using cross-linking agents known for intermolecular modification, such as bifunctional cross-linking agents like butadiene diepoxy, divinyl sulfone, diisocyanate, particularly hexamethylene diisocyanate, cyclohexyl diisocyanate, and 2,5-bisisocyanatobenzol sulfonic acid, di-N-hydroxy succinimidyl ester, diimidoester, or dialdehyde, particularly glyoxal, glycol aldehyde that reacts analogously, or glutardialdehyde may be used.

Furthermore, products which are polymerized in this manner and pegylated with a polyethylene glycol or suitable derivatives thereof may be used. This includes, for example, polyethylene oxide, polypropylene oxide, or a copolymer of ethylene oxide and propylene oxide, or an ester, ether, or ester amide thereof. It may be suitable if the covalently linked polyalkylene oxide has a molar mass of 200 to 5000 g/mol.

For covalent linking of the polyalkylene oxides, those derivatives of polyalkylene oxide that contain a linking agent already covalently bound with a functional group, thereby allowing a direct chemical reaction with amino, alcohol, or sulfhydryl groups of the hemoglobins, forming covalent links of the polyalkylene oxides may be suitable, for example polyalkylene oxides with reactive N-hydroxy succinimidyl ester, epoxy (glycidyl ether), Idehyde, isocyanate, vinyl sulfone, iodacetamide, imidazolyl formate, tresylate groups, and others. Many such monofunctionally activated polyethylene glycols are commercially available.

If modified oxygen carriers are used, modified cross-linked (intramolecular or intermolecular), or cross-linked and pegylated hemoglobin products having an average molecular weight of 250,000 to 1,500,000 g/mol, or myoglobin products having an average molecular weight of 50,000 to 750,000 g/mol, are preferred.

According to the particular preferred embodiment freshly isolated hemoglobin or myoglobin of human or animal origin, in particular of porcine origin is used for preparation of the composition.

According to the present invention at least 40% of the oxygen binding sites of the oxygen carrier are charged with a non-$O_2$ ligand. Preferably at least 50%, preferably at least 60%, more preferred at least 70%, even more preferred at least 80%, particularly preferred at least 90% or 95% of the oxygen carrier, e.g. hemoglobin or myoglobin is provided in ligand-charged form. This charge may already be applied during isolation of the carrier or after its further purification, however, it is particularly preferred to carry out the isolation of the oxygen carrier in its protected form, which means that during isolation or purification the ligand is provided to/contacted with the oxygen carrier.

The non-$O_2$ ligand preferably is carbon monoxide (CO) or nitrogen monoxide (NO) or a mixture thereof. Both ligands have a high affinity for the hemoglobin/myoglobin $O_2$ bindig site(s) and serve as a protector against oxidation of the central $Fe^{2+}$ Ion of the heme. According to the most preferred embodiment the non-$O_2$ ligand is CO.

The charged oxygen carrier(s) is/are preferably dissolved in an aqueous or organic medium, wherein an aqueous solution is preferred, in an amount of 0.1 to 35 wt.-%, preferably 0.1 to 20 wt.-%, more preferred 0.1 to 15 wt.-%, to be ready for application.

The composition according to the present invention further comprises at least one further additive, preferably selected from the group comprising electrolyte(s), stabilizer (s), anti-flocculant(s), preservative(s), anti-coagulants, pH buffering agent(s), solvent(s), antioxidant(s) and film-forming agent(s), ointment ingredients, oils, greases or fats or crosslinking agents; more preferred selected from electrolyte(s), stabilizer(s), anti-flocculant(s), preservative(s) and pH buffering agent(s). Most preferred the composition is in form of a solution and comprises at least an electrolyte and optionally a stabilizer.

The solution may comprise physiologically compatible electrolytes, such as salts, in suitable or desired amounts. The electrolytes may be present in amounts of 0.1 to 30 wt.-%, preferably 0.1 to 10%, but preferably are present in a physiological concentration, respectively. Preferably the composition comprises a salt in the before mentioned amounts, like e.g. NaCl, KCl, $NH_4Cl$, $CaCO_3$, $Na_2CO_3$, K$_2$O$_3$, MgSO$_4$,1 Na$_2$SO$_4$, CaCl$_2$, MgCl$_2$, sodium citrate, sodium lactate or mixtures of the mentioned or similar without being restricted to these examples. The most preferred salt is NaCl, particularly in a concentration of 0.9% (isotonic solution).

According to the invention it is particularly preferred that the composition comprises a compound acting as a stabilizer and/or anti-flocculant for proteins in particular for the oxygen carrier like hemoglobin/myoglobin, such as N-acetyl cysteine, cysteine, N-actyl methionine, methionine, non-chaotropic salts, polyols, like sugars, preferably disaccharides, and amino acids preferably each in amounts of 0.001 wt.-% to 20 wt.-%.

The polyols which may be employed are preferably low molecular weight polyols although polymeric derivatives may be employed. Such polyols include ethylene glycol, glycerol, erythritol and mannitol. Cyclic polyols which may be employed incorporate one or more alicyclic rings and may have at least one side chain. Preferred polyols include disaccharides and sugar alcohols, for example lactitol, sorbitol and inositol. Compounds having 2 to 10 hydroxyl groups are preferred. The amount of the polyol may be in the preferred range 0.001 to 20% more preferably 1 to 15% most preferably 2 to 10% w/v.

Further the protein stabilizer additive may be selected from a tris(hydroxymethyl)methyl compound of formula 1;

(HOCH$_2$)$_3$C—R (1) wherein R is: C$_1$-C$_4$ alkyl, substituted C$_1$-C$_4$ alkyl, NH$_2$, NHC(CH$_2$OH)$_3$, C$_1$-C$_4$ hydroxyalkyl; C$_1$-C$_4$ alkyl carboxylate, NR$^1$R$^2$ (wherein R$^1$ and R$^2$ may be independently: H, C$_1$-C$_4$ alkyl, C$_1$-C$_4$ alkyl sulphonate, C$_1$-C$_4$ hydroxyalkyl sulphonate). Examples of preferred compounds of formula (1) include: tris(hydroxymethyl) ethane; 1,1',1"-tris(hydroxymethyl)propane; tris(hydroxymethyl)aminomethane or salts thereof for example chloride, maleate, phosphate, succinate salts; 1,3 bis[tris(hydroxymethyl)methylamino]propane; bis(2hydroxyethyl)amino-tris (hydroxymethyl)methane; N [tris(hydroxymethyl)methyl]-2-aminoethane sulphonate; N [tris(hydroxymethyl)methyl]-3-aminopropane sulphonate; N [tris(hydroxymethyl) methyl]-3-amino-2-hydroxypropane sulphonate; N-[tris (hydroxymethyl)methyl]-glycine. Said compounds as well may be added in the preferred range of 0.001 to 20% more preferably 1 to 15% most preferably 2 to 10% w/v.

Further the protein stabilizer additive may be selected from a polyelectrolyte. The polyelectrolyte may be a cationic or anionic polyelectrolyte. Amphoteric polyelectrolytes may also be employed. The cationic polyelectrolyte is preferably a polymer with cationic groups distributed along the molecular chain.

The cationic groups, which are preferably quaternary ammonium derived functions, may be disposed in side groups pendant from the chain or may be incorporated in it. Examples of cationic polyelectrolytes include: Copolymers of vinyl pyrollidone and quaternary methyl methacrylate e.g. Gafquat series (755N, 734, HS-100) obtained from ISP; substituted polyacrylamides; polyethyleneimine, polypropyleneimine and substituted derivatives;

polyamine homopolymers (Golchem CL118); polyamine co-polymers (e.g. condensates of epichlorohydrin and mono or dimethylamine); polydiallyl dimethyl ammonium chloride (polyDADMAC); substituted dextrans; modified guar gum (substituted with hydroxypropyltrimonium chloride); substituted proteins (e.g. quaternary groups substituted on soya protein and hydrolysed collagen); polyamino acids (e.g. polylysine); low molecular weight polyamino compounds (e.g. spermine and spermidine). Natural or artificial polymers may be employed.

Cationic polyelectrolytes with MW 150 to 5,000,000, preferably 5000 to 500,000, more preferably 5000 to 100,000 may be employed. An amount of 0.01 to 10% is preferred, more preferably 0.1 to 2%, especially 0.05 to 5% w/v.

The anionic polyelectrolyte is preferably a polymer with anionic groups distributed along the molecular chain. The anionic groups, which may include carboxylate, sulphonate, sulphate or other negatively charged ionisable groupings, may be disposed upon groups pendant from the chain or bonded directly to the polymer backbone. Natural or artificial polymers may be employed.

Examples of anionic polyelectrolytes include: Gantrez (Series, AN-series); alginic acid and salts; carboxymethyl celluloses and salts; substituted polyacrylamides (e.g. substituted with carboxylic acid groups); polyacrylic acids and salts; polystyrene sulphonic acids and salts; dextran sulphates; substituted saccharides e.g. sucrose octosulphate; heparin. Anionic polyelectrolytes with MW of 150 to 5,000, 000 may be used, preferably 5000 to 500,000, more preferably 5000 to 100,000. An amount of 0.01% to 10% is preferred especially 0.05 to 5% more especially 0.1 to 2% w/v.

A particular preferred stabilizer is N-acetyl cysteine in an amount of 0 to 10%, preferably 0.01 to 5%.

Further the composition may contain any preservative like e.g. phenoxyethanol, isothiazoline, sorbic acid or any other suitable preservative known to skilled persons.

The composition may further preferably comprise any buffering agent. All of the commonly known buffering agents may be used, like Tris/HCl, K$_2$HPO$_4$/KH$_2$PO$_4$, Na$_2$HPO$_4$/NaH$_2$PO$_4$, MOPS (3-(N-morpholino)propane-sulfonic acid), HEPES (4-2-hydroxyethyl-1-piperazineethanesulfonic acid), TAPS (3-{[tris(hydroxymethyl) methyl]amino}propanesulfonic acid), Bicine (N,N-bis(2-hydroxyethyl)glycine), Tricine (N-tris(hydroxymethyl) methylglycine), TES (2-{[tris(hydroxymethyl)methyl] amino}ethanesulfonic acid), PIPES (piperazine-N,N'-bis(2-ethanesulfonic acid)), SSC (saline sodium citrate), MES (2-(N-morpholino)ethanesulfonic acid) without being limited to these.

Suitable solvents in the composition according to the invention are preferably water or aqueous solutions, organic solvents like alcohol, preferably ethanol, or polyethyleneglycol (PEG). Mixtures of said solvents as well can be used. A particularly preferred solvent is water or an aqueous solution, in particular if the composition is provided in liquid form.

Antioxidants useful for the present composition may be e.g. vitamin C, vitamin E, flavonoids, carotinoids, or salts or derivatives thereof.

Preferred film-forming agents are such agents commonly used in cosmetic application, like e.g. Acrylamide/Sodium, Acrylate Copolymer, Acrylates/Acrylamide Copolymer, Butyl Ester of PVM/MA Copolymer, Carboxymethyl Chitin, Chitosan, Hydroxypropyl Cellulose, Polyquaternium-36, PVP, PVP/VA Copolymer, VA/Crotonates Copolymer or Vinyl Caprolactam/PCP/Dimethylaminoctyl Methylacrylate Copolymer.

All the above mentioned additives may be present in an amount of 0 to 20, preferably 0.001, 0.01, 0.05 or 0.1 to 10, more preferably 0.5 to 5% (w/v), if not otherwise stated above.

If desired, further additives may be present, in particular in an amount of 0 to 20, preferably 0.1 to 20, preferably 0.2 to 15, particularly 0.5 to 10 wt.-%. Preferred additives are nutrients for cells. They can be selected from glucose, e.g.

in amounts of 0.1 to 5 wt.-%, insulin in amounts of up to 25 IU/ml, the natural amino acids, in particular cysteine, e.g. 0.1 to 5 wt.-%, or tissue factors, such as interleukins in physiological amounts, up to a 10-fold amount thereof.

The composition of the present invention can be provided in form of an aqueous or organic solution, a lotion, a cream, a gel, an ointment or a powder, or said oxygen carrier compound or composition is comprised in a plaster, bandage or dressing.

If the composition comprising the oxygen carrier is provided in form of a lotion, cream or ointment, said composition preferably comprises any greasy, fatty, waxy or oily ingredient. Such ingredients are well known in the art and may be for example any cosmetically acceptable oil, wax, grease or fat commonly used in crèmes, lotions, emulsions or ointments.

Suitable fatty or oily components are animal and/or vegetable fats and oils, such as olive oil, sunflower oil, purified soya oil, palm oil, sesame oil, rapeseed oil, almond oil, borage oil, evening primrose oil, coconut oil, shea butter, jojoba oil, sperm oil, beef tallow, neatsfoot oil and lard. The composition may also comprise further treatment constituents, such as, for example, fatty alcohols having 8-30 C atoms. The fatty alcohols used here can be saturated or unsaturated and straight-chain or branched. Suitable examples are, decanol, decenol, octanol, octenol, dodecanol, dodecenol, octadienol, decadienol, dodecadienol, oleyl alcohol, ricinol (sic) alcohol, erucic alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well the guerbet alcohols thereof, without being limited to the mentioned. The fatty alcohols preferably originate from natural fatty acids, and are usually prepared from the corresponding esters of the fatty acids by reduction. Furthermore, fatty alcohol fractions that are formed from naturally occurring fats and fat oils by reduction can be used, such as, for example, beef tallow, peanut oil, colza oil, cottonseed oil, soya oil, sunflower oil, palm kernel oil, linseed oil, maize oil, castor oil, rapeseed oil, sesame oil, cocoa butter and cocoa fat.

Further possible ingredients are ceramides, ceramides being understood to be N-acylsphingosines (fatty acid amides of sphingosine) or synthetic analogues of such lipids (so-called pseudo-ceramides), which clearly improve the water retention capacity of the stratum corneum.

phospholipids, for example soya lecithin, egg lecithin and cephalins

Vaseline, paraffin, mineral oils, mineral waxes fatty oils, fats, waxes and other natural and synthetic fatty bodies, preferably esters of fatty acids with alcohols having a low C number, for example with isopropanol, propylene glycol or glycerol, or esters of fatty alcohols with alkanoic acids having a low C number or with fatty acids;

alkyl benzoates;

silicone oils, such as dialkyl- and alkylaryl-siloxanes, such as dimethylpolysiloxanes, diethylpolysiloxanes, diphenylpolysiloxanes and methylphenylpolysiloxane, as well as the alkoxylated and quaternised derivatives thereof and.mixed forms therefrom.

As fatty esters such of saturated and/or unsaturated, branched and/or straight-chain alkanecarboxylic acids having a chain length of 3 to 30 C atoms and saturated and/or unsaturated, branched and/or straight-chain alcohols having a chain length of 3 to 30 C atoms, from the group of esters of aromatic carboxylic acids and saturated and/or unsaturated, branched and/or straight-chain alcohols having a chain length of 3 to 30 C atoms can be used. Preferred ester oils are isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters, for example, jojoba oil.

As fatty/waxy components fats and fat-like substances with a wax-like consistency may also be used as waxes. These include, inter alia, fats (triglycerides), mono- and diglycerides, natural and synthetic waxes, fat and wax alcohols, fatty acids, esters of fatty alcohols and fatty acids and fatty acid amides or mixtures of these substances.

Fats usually invention are understood to be triacylglycerols, i.e., the triple esters of fatty acids with glycerol. The triacylglycerols preferably contain saturated, unbranched and unsubstituted fatty acid components. They may also be mixed esters, i.e., triple esters of glycerol with various fatty acids. So-called hardened fats and oils obtained by partial hydrogenation may be used in accordance with the invention and are particularly suitable as consistency factors. Vegetable hardened fats and oils, for example, hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, are preferred.

Suitable fats are, inter alia, the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the trademark Cutina(R) HR. Glycerol tristearate, glycerol tribehenate (for example Syncrowax(R) HRC), glycerol tripalmitate or the triglyceride mixtures known under the trademark Syncrowax(R) HGLC are also suitable providing the melting point of the wax component or the mixture is 30 degrees centigrade or higher.

Examples of suitable wax components are, in particular, mono- and diglycerides and mixtures of these partial glycerides. The fatty alcohols suitable for use as a wax include $C_{12-50}$ fatty alcohols. The fatty alcohols may be obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. Usually, saturated unbranched fatty alcohols are preferred, however, unsaturated, branched or unbranched fatty alcohols may also be used as wax component. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols) or the partly branched alcohols from the oxosynthesis (Dobanols) may also be used. $C_{14-22}$ fatty alcohols marketed for example by Cognis Deutschland GmbH under the name of Lanette(R) 16 ($C_{16}$ alcohol), Lanette(R) 14 ($C_{14}$ alcohol), Lanette(R) 0 ($C_{16/18}$ alcohol) and Lanette(R) 22 ($C_{18/22}$ alcohol) are particularly suitable for the purposes of the invention. Fatty alcohols give the compositions a dryer feeling on the skin than triglycerides.

$C_{14-40}$ fatty acids or mixtures thereof may also be used as wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes suitable for use are further, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. Itit can be of advantage to use hydrogenated or hardened waxes. Natural waxes also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable include, for example, wax-like polyalkylene waxes and polyethylene glycol waxes.

The wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Examples of esters such as these include, for example, $C_{16-40}$ alkyl stearates, $C_{20-40}$ alkyl stearates (for example Kesterwachs(R) K82H), $C_{20-40}$ dialkyl esters of dimer acids, $C_{18-38}$ alkyl hydroxystearoyl stearates or $C_{20-40}$ alkyl erucates. Other suitable wax components which may be used are $C_{30-50}$ alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

A further application form for the compound or composition of the present invention is in form of a gel. In such an application form the composition comprises any ingredient commonly used in gelly compositions, i.e. gelling agents like polymeric polysaccharides (e.g. cellulose or derivatives thereof, starch or derivatives thereof), proteins (e.g. gelatine) or polyacrylates. Examples of suitable gelling compounds are Carbomer, Carmellose-Natrium (INCI-Cellulose Gum), Hydroxymethylcellulose, Hydroxyethylcellulose and Hydroxypropylcellulose, gelling salicylic acid, a combination of Chitosane and EDTA, polyacrylate-polyalkylacrylat-Crosspolymer (e.g. Carbomer 1342, Pemulen®) or ammonium acryloyldimethyltaurat/vinylpyrrolidone copolymer (Aristoflex® AVC).

Furthermore the compound or composition of the present invention can be provided in form of a powder, comprising besides the oxygen carrier other suitable powdery components. Commonly used powder components are well known in the art and include talc, silica, starch (e.g. from corn, rice etc.), silicon dioxide, titanium dioxide, zinc oxide, without being limited to the mentioned.

The compound or composition as defined herein preferably is applied to a body site or body area where due to a disease or any disorder the body develops an unpleasant feeling. Such a body site or area might be any body surface, in particular body surface reachable without cutting the skin. Such a surface might be the whole epidermal surface, i.e. the external surface of the body, but also the oral cave, the inside of an eyelid, the nares, the reachable area inside the ears etc. Preferably the surface of the body means the external surface.

The compound or composition according to the invention is applied to the body surface at a site or area where the body developed an unpleasant feeling due to a disease or disorder. The compound or composition may be applied to said surface site or area by spraying a solution, spreading a cream or lotion, rubbing an ointment or gel or applying a powder or by any other suitable method. Further, the compound or composition can be included into a plaster, a bandage or a dressing and can be contacted with the body surface by applying said plaster, bandage or dressing to said surface.

The body site or body area treated with the compound or composition according to the present invention preferably is one which shows any result of affection of a disorder or disease, preferably the body surface shows blebs, blisters, pimples, rash, red patches, or wheals. Such body reactions commonly are observable when the body is affected e.g. by a virus, in particular when the body responses to virus proliferation of e.g. a Herpes virus. The present invention therefore is directed to the treatment of an unpleasant feeling elicited by the reaction of the body to disorders and diseases (immune response) resulting in visible features on the body surface, in particular on the skin. Such visible features can be one or more of them cited before.

The present invention is particularly suitable for the treatment of an unpleasant feeling elicited by the virus proliferation of a virus of the Herpes type. As described above Herpes viruses after a first infection (e.g. a Herpes zoster infection resulting in chicken pox or a Herpes simplex infection resulting in lip blisters) remain in a latent form in a living body and may proliferate later again, thus, re-eliciting symptoms like itching and painful blisters. In particular the Herpes zoster virus may result in periodically or irregularly occurring "attacks" of shingles, a painful and persistent disease, the Herpes simplex virus may result in periodically or irregularly occurring "attacks" of lip blisters. It was surprisingly found that the application of an oxygen carrier, in particular a compound of the hemoglobin or myoglobin type, can alleviate both the itching and the pain in the affected areas if applied to said area. Therein it appears sufficient to provide a thin film of a composition comprising the oxygen carrier to the affected area to decreasing the intensity of the unpleasant feeling of e.g. itching, stinging, burning or pain.

Due to the decrease of the unpleasant feeling resulting from the disease or disorder, the patient tends less to scratch the affected areas, thus the body surface will be less injured and can heal better without developing scars. Further, scratching often results in a further immune response of the body, e.g. the histamine delivery, increasing the itching or stinging feeling, and also resulting in swelling of the affected area. All these characteristics can be diminished by applying the oxygen carrier to the affected area, thereby increasing locally the oxygen content.

According to the present invention an oxygen carrier is used, which preferably is isolated from whole blood of a human or animal, preferably from pigs.

For use according to the invention the oxygen carrier may be isolated from blood of a human or animal and is further purified to be essentially free of plasma and cellular membrane constituents.

With "essentially free" is meant that the considered compound or composition doesn't comprise more than 20%, preferably not more than 10%, even more preferred not more than 5% and particularly preferred not more than 2% or less than 1% of the mentioned undesired compound(s).

The purification can comprise any suitable means or method steps, like e.g. selective lysis or precipitation, centrifugation, ultracentrifugation, fractionated centrifugation, chromatography methods like anion exchange chromatography, size exclusion chromatography, affinity or adsorption chromatography, gel filtration or molecular sieve chromatography, or dialysis, without being restricted to these examples, as far as by the applied methods the oxygen carrier is denaturated as less as possible. Preferably during isolation and purification the oxygen carrier remains essentially in solution.

When the oxygen carrier is isolated from whole blood, it is preferred that either the cells comprising the oxygen carrier are separated from other blood components or said cells are selectively lysed to deliver the (soluble) oxygen carrier into solution and thereafter the non-soluble components are separated. A combination of the two methods as well is suitable. The lysis of the oxygen carrier containing cells may be carried out by any suitable lysis method, e.g. chemical lysis, osmotical lysis, mechanical lysis, thermal lysis or similar.

Cell debris may be separated by any suitable means or method. This includes e.g. centrifugation, filtration, sedimentation and decantation, dialysis or any similar method.

For separating non-lysed cells or the cell debris from the solved oxygen carrier a common method is pelletation of the solid material. For example a centrifugation step may be carried out. Centrifugation with 2 to 5000×g usually is sufficient for pelleting cells and cell debris.

For pelleting further non-solved components, e.g. any precipitate developed during the purification process, at any time during the purification process further centrifugation steps may be carried out, in particular centrifugation steps using higher forces, up to ultracentrifugation with up to $10^6 \times g$.

The purification of the oxygen carrier containing solution additionally or as an alternative to any centrifugation step may comprise at least one filtration step, preferably at least two, three or more filtration steps. This can be carried out either by using at least one, preferably at least two, more preferably at least three filters (if more than one filter is used in the present application we use the term "filter cascade"), or by one, two, three or more separate filtration steps.

Said filter cascade or the different filtering steps may include two, three, four, five or more filters of different type, different material and or different pore sizes. Further a deep bed filter like e.g. glass wool or similar may be used, preferably as a first filter material to retain coarse cell debris. If more than one filter is used, it is preferred to use filters providing different pore diameters in decreased order. For example, if three different filters are used, the first filter (after the deep bed filter) may have an average pore size of 1 to 0.5 µm, the second filter may have a pore size of 0.7 to 0.3 µm and the third a pore size of 0.4 to 0.1 µm, wherein independent from the overlapping ranges cited before the following filter in any case has a smaller pore size than the filter prior to that. By said filtering step(s) solid and precipitated material having a larger size than the pore size of the used filters is essentially removed.

Further an ultrafiltration step may be included in the purification process for purifying the oxygen carrier(s). By such an ultrafiltration step, non-desired solved macromolecules can be separated. Preferably the size exclusion limit is selected to separate macromolecules which are bigger (larger, higher molecular weight) than the desired oxygen carriers, accordingly said macromolecules are retained by the filter. Due to the molecular weight of hemoglobin of about 64,000 Dalton the size exclusion limit of the ultrafiltration filter should be higher. To make sure that the yield of hemoglobin is not decreased by the ultrafiltration step, it is preferred to select the size exclusion of the filter at about 100,000 Dalton, preferably at about 200,000 Dalton, more preferred at about 300,000 Dalton without being restricted to these values.

Additionally or as an alternative any suitable chromatography step can be carried out. A particularly preferred type of chromatography is ion exchange or size exclusion chromatography.

The same result may be obtained by a dialysis step using a dialysis membrane providing the above mentioned size exclusion limits, allowing the oxygen carrier to pass, but retaining the macromolecules having a higher molecular size.

To lower the amount of small molecular weight compounds in solution an additional dialysis step may be carried out using a dialysis membrane having a size exclusion limit of about 50.000 Dalton, allowing smaller molecules to pass, but retaining the oxygen carrier.

To diminish the virus and/or microorganism contamination in the composition it is particularly preferred to include a step of virus content degradation in the purification process. The virus content is reduced by this step, preferably to a burden of less than 10, preferably less than 5, more preferably less than 2 virus particles per ml, and even more preferred to 0. In this step it is preferred that the solution comprising the oxygen carrier is passed through a virus content degradation filter ("virus filter"). Such filters are commonly known and available on the market. Examples are Sartorius Virosart® CPV, Planova® 15N,20N, Millipore Viresolve® NFP or PALL Pegasus® Grade LV6, without being limited to these. Alternatively or additionally, preferably after the passage through the filter, a treatment with UV light, in particular UV light of a wavelength of 245 nm may be applied to dispatch any remaining viruses.

Optionally at any stage during the process of isolation of the oxygen carrier at least one heating step may be carried out. This step comprises the heating of the oxygen carrier containing suspension or solution during the isolation procedure to a temperature in the range of 40 to 85° C., preferably 60 to 80° C., more preferred in the range of 65 to 75° C. The heating step is carried out preferably for 10 min to 6 hours, preferably for 20 min to 4 hours and most preferred for 30 min to 3 hours and may comprise several different temperatures within the before mentioned range.

According to the process of the present invention it is preferred that the oxygen carrier remains in solution during the whole purification process. Further it is preferred that the oxygen carrier remains in solution during the whole purification process and during preparation of the composition of the present invention. This means that it is preferred that the oxygen carrier is not precipitated in the process of the present invention and accordingly remains in its natural three-dimensional structure as present in its natural environment.

In a particular preferred process according to the present invention the process for purifying an oxygen carrier from whole blood comprises at least the steps:
(a) separating plasma of the whole blood
(b) lysing the red blood cells
(c) charging the oxygen carriers with the ligand
(d) heating the sample to a temperature in the range of 40 to 85° C.
(e) separating the oxygen carrier from any non-desired blood components.

By these steps an oxygen carrier containing solution is obtainable which can be used for the preparation of the composition of the present invention. In particular the oxygen carrier containing solution obtainable by these steps may be concentrated to a desired amount of the oxygen carrier and to this solution the at least one further ingredient(s) is/are added to obtain the composition of the present invention.

Step (a) of the present method can be carried out by any of the commonly used methods for separating plasma from whole blood, preferably by centrifugation or filtration. By centrifugation for about 30 min at about 2000 to 5000 rpm, e.g. 4000 rpm red blood cells are pelleted, whereas soluble compounds and white blood cells remain predominantly in the supernatant. By repeating resuspension and pelleting of the red blood cells e.g. 2 to 5 times, separation of the red blood cells from the undesired blood compounds can be increased.

Step (b) is preferably carried out by adding water, preferably distilled water or a suitable sub-isotonic buffer, preferably a phosphate buffer, to the thickened blood of step (a). After lysing the red blood cells with water or a sub-isotonic buffer preferably a salt is added to the solution/suspension to obtain physiological concentration of said salt in solution. Preferably NaCl is added to an amount of 0.9% in solution.

Step (c) may be carried out after step (a), after step (b), after step (d) or after step (e), but is preferably carried out at least after step (b). It is particularly pointed out that step (c) is not necessarily carried out immediately as a next step after step (b), but as well can be carried out or repeated after step (d), after step (e) or any following treatment steps. The charging of the oxygen carrier in the solution/suspension may be carried out by introducing gas in the solution/suspension, preferably CO or NO gas or a mixture thereof. In a preferred embodiment CO gas is introduced into the solution/suspension for a time period long enough to obtain a >90% saturation in the solution/suspension, preferably a >95% saturation.

Step (d) may be carried out after step (a), after step (b), after step (c) or after step (e), but is preferably carried out after step (c). Further the heating can be repeated during the isolation procedure. This step comprises the heating of the oxygen carrier containing suspension or solution during the isolation procedure to a temperature in the range of 40 to 85° C., preferably 60 to 80° C., more preferred in the range of 65 to 75° C. The heating step is carried out preferably for 10 min to 6 hours, preferably for 20 min to 4 hours and most preferred for 30 min to 3 hours and may comprise several different temperatures within the before mentioned range.

In step (e) the oxygen carrier is purified from further non-desired ingredients still contained in solution, like non-lysed cells, cell debris, any precipitate or other non-soluble ingredients. Further the oxygen-carrier may be further purified by separating at least partially non-desired soluble compounds, like e.g. soluble macromolecules or soluble compounds having low molecular weight.

Accordingly said step (e) may include several single steps, like filtration, ultrafiltration, centrifugation, ultracentrifugation, chromatography, dialysis using different types of dialysis membranes providing different size exclusion limits, washing steps, concentration of the oxygen carrier content etc. Any of the methods cited above may be included in this purification step.

Preferably at least one centrifugation and/or at least one filtration step is comprised in step (e). E.g. the lysate may be spinned in a centrifuge to separate remaining cells and cell debris or it is filtered e.g. by a filter cascade as described above. The lysate can be as well first centrifuged and thereafter filtered, or it may be filtered in a first step through a deep bed filter and thereafter through at least one filter or a filter cascade. By the centrifugation or the deep bed filter the handling during any following filtering steps is simplified due to less material settling on and clogging the filter(s). If not a filter cascade is used, it is preferred that at least one filter is used allowing to retain essentially all of the solid materials contained in the suspension and allowing to pass all the solved components. In a more preferred embodiment at least one of the used filter(s) is able to retain as well microorganisms, acting as a sterile filter. Further preferred an ultrafiltration step and/or a step for diminishing the virus and/or microorganism content of the solution can be carried out. Accordingly it is preferred that after step (e) the oxygen carrier containing solution is essentially free of any non-solved particles, flocks or precipitate.

In step (e) additionally to any of the steps/methods cited above the solution comprising the desired oxygen carrier may be washed and/or concentrated. By "washing" is meant that molecules smaller than the desired oxygen carrier (having lower molecular weight) are separated, preferably by adding the same or a multifold (e.g. 5 to 10 fold) amount of an isotonic solution to the oxygen carrier containing solution and thereafter filtering the obtained (diluted) solution by a filter retaining the oxygen carrier and allowing smaller molecules to pass. For washing the solution preferably a 0.9% NaCl solution is used. The washing step may be repeated 2 or 3 or 4 or 5 or up to 10 times. A preferred embodiment is exemplified by the use of a filter having a size exclusion limit of 5,000 Dalton, 10,000 Dalton or 20,000 Dalton, allowing smaller molecules to pass. In this step the oxygen carrier containing solution (preferably after washing) may be concentrated to a desired concentration of the oxygen carrier, e.g. to a concentration of 50 g/l, 100 g/l or 200 g/l without being restricted to these amounts. Any desired concentration can be obtained either by concentrating by filtration or by adding 0.9% NaCl or a similar isotonic solution.

The so obtainable oxygen carrier containing solution can then be used to prepare the composition of the present invention by adding the at least one further ingredient described above to the solution in the desired amount.

In a preferred embodiment the composition of the present invention is prepared by adding to the oxygen carrier containing solution at least a preservative, preferably a pharmaceutically acceptable preservative like e.g. phenoxyethanol, parabenes, sodium benzoate, benzyl alcohol, hexachlorophen and an antioxidant and/or stabilizer like e.g. N-acetylcysteine, sodium octanoate, N-acetyl-l-tryptophanate, N-acetyl-methioninate, vitamin E, vitamin C, methyl prednisolone or mannitol. Additionally any of the further ingredients described above may be added additionally.

The finished composition may be sterilized again, if desired, e.g. by heating, filtration, centrifugation, addition of preservatives, vapour application, gas application or UV-application or a combination of at least two of them, preferably by a further sterile filtration step and is preferably filled in sterile containers or sterile bags for storing.

According to a preferred embodiment the sterile bags are positioned in an aerosol can for later use. One preferred example can be a Bag-on-Valve system, comprising a bag, e.g. a laminated aluminium bag and an aluminium or tin plate aerosol can. Due to the separation of product and propellant, Bag-on-Valve can be used with compressed air or nitrogen at a pressure e.g. from 2 to 9 bar. Further, other suitable systems for applying a liquid, gel, cream, lotion or ointment can be used, allowing the further storage of the hemoglobin comprising composition under non-oxidizing conditions. Examples are commonly used aerosol cans, airless dispensers, airless pump dispensers, airless tubes or spraying containers or spraying flasks, as far as such devices work without sucking back air after an application use. Another example of providing the composition of the present invention, either in liquid, gelly, creamy, pasty or powdery form is a one-unit-package, i.e. the amount of the composition suitable for one application is provided in a receptacle of glass, plastic or any other suitable package material (e.g. an ampulla), or in form of a pouch, sachet, package or blow-formed container of any suitable and commonly used (non oxygen permeable) material.

The composition of the present invention has the clear advantage of increased stability of the oxygen-carrier due to its non-oxidized status based on the charge with the CO or NO ligand resulting in a good preparation and storing stability. Further the composition is easy to apply and good to handle and provides a safe and effective approach to improve any unpleasant feeling by facilitated diffusion mediated by the oxygen carrier agent.

The composition of the present invention preferably is applied externally. Depending on the state of the surface to be treated, it is applied on, preferably sprayed on the surface area, e.g. in form of a fine spray.

EXAMPLES

Example 1: Preparation of the Oxygen Carrier and a Composition Comprising Same Hemoglobin was isolated from whole blood of pigs by separating the red blood cells from serum, lysing the collected red blood cells, pelleting cell debris, charging the hemoglobin with CO by introducing CO gas until saturation of the liquid sample is obtained, heating the solution, carrying out several filtration steps, including a virus filtration step and washing the obtained hemoglobin solution by adding twice a 2-fold volume of 0.9% saline and filtering the solution.

A ready-to-use composition for treatment of a body surface was prepared, comprising 10% of purified and stabilized hemoglobin, 0.05% N-acetyl cysteine and 0.7% phenoxy ethanol in 0.9% NaCl. The composition was charged again with CO gas, separated into 10 portions and packaged into an aerosol can, respectively.

Example 2: Comparison of Charged/Non-Charged Hemoglobin

A) A charged hemoglobin-spray was prepared according to Example 1

A ready-to-use composition for treatment of a body surface was prepared, comprising 10% of purified and stabilized hemoglobin, 0.05% N-acetyl cysteine and 0.7% phenoxy ethanol in 0.9% NaCl. The composition was charged again with CO gas, separated into 20 portions and packaged into an aerosol can, respectively.

The composition can be stored between 4° C. and room temperature for months to years.

B) A second portion of the pig whole blood was treated as in Example 1 with the exception that no CO charging was carried out. During the heating step a considerable amount of hemoglobin precipitated. The following filtration steps were difficult to carry out. The yield of purified hemoglobin per liter whole blood decreased to less than 30% of the yield when the CO charging is carried out before heating. This shows that charging the samples with CO during preparation stabilizes the hemoglobin in a way that during a heating step considerably less hemoglobin precipitates.

A ready-to-use composition for treatment of a body surface was prepared, comprising 10% of purified hemoglobin, 0.05% N-acetyl cysteine and 0.7% phenoxy ethanol in 0.9% NaCl. The composition was portioned and packaged into aerosol cans, respectively.

Example 3

Samples of compositions prepared according to Example 2A) or Example 2B), respectively, were examined considering the $O_2$ charge of the samples as well as the production of methemoglobin, a species which is unable to bind $O_2$. Furthermore methemoglobin affects hemoglobin molecules in the immediate vicinity in a way that these can still bind $O_2$, but cannot release it no more.

All the samples of Table 1 were diluted 1:1 with a 0.9% NaCl solution. Samples 3.1 to 3.5 were measured immediately after dilution (storing of samples 3.4 and 3.5 was at room temperature before dilution). Gas treatment was as follows: 6 ml of said diluted solution were transferred into a 30 ml glass flask each. Gas treatment was carried out by filling the glass flask completely with the respective gas, closing the flask and pivoting the sample for 30 sec. All the samples were stored for the mentioned time period at 30° C. The samples were treated according to the conditions described in Table 1 and the total amount of hemoglobin (hemoglobin+methemoglobin), the oxygen content, the methemoglobin content and optionally the CO content was measured.

TABLE 1

| Example | sample | treatment | totalHb g/dL | $O_2$ % | CO % | MetHb % |
|---|---|---|---|---|---|---|
| 3.1 | Freshly prepared comp. according to Example 2A) | none | 5.5 | 1.7 | 96.3 | 3.9 |
| 3.2 | Freshly prepared comp. According to Example 2B) | none | 5.7 | 26.8 | | 5.1 |

TABLE 1-continued

| Example | sample | treatment | totalHb g/dL | $O_2$ % | CO % | MetHb % |
|---|---|---|---|---|---|---|
| 3.3 | Composition of Example 2A), stored for 3 month (10° C.) | none | 5.9 | 1.8 | 96.5 | 3.8 |
| 3.4 | Composition of Example 3.2 | Stored for 24 h | 5.6 | 26.9 | | 11.2 |
| 3.5 | Composition of Example 3.2 | Stored for 48 h | 5.5 | 27.0 | | 17.0 |
| 3.6 | Composition of Example 3.3 | 0.5 h $O_2$ | 5.8 | 13.7 | 84.7 | 4.4 |
| 3.7 | Composition of Example 3.3 | 1 h $O_2$ | 5.7 | 19.6 | 79.1 | 4.2 |
| 3.8 | Composition of Example 3.3 | 2 h $O_2$ | 5.8 | 25.7 | 73.1 | 4.3 |
| 3.9 | Composition of Example 3.3 | 3 h $O_2$ | 5.9 | 30.7 | 68.1 | 4.2 |
| 3.10 | Composition of Example 3.3 | 24 h $O_2$ | 5.7 | 33.5 | 59.6 | 9.8 |
| 3.11 | Composition of Example 3.3 | 48 h $O_2$ | 5.8 | 32.5 | 55.9 | 15.5 |
| 3.12 | Composition of Example 3.3 | 72 h $O_2$ | 5.7 | 31.7 | 55.8 | 16.0 |
| 3.13 | Composition of Example 3.3 | 0.5 h $CO_2$ | 5.8 | 4.0 | 91.8 | 5.7 |
| 3.14 | Composition of Example 3.3 | 1 h $CO_2$ | 5.7 | 6.0 | 90.0 | 5.7 |
| 3.15 | Composition of Example 3.3 | 2 h $CO_2$ | 5.9 | 9.2 | 86.7 | 5.8 |
| 3.16 | Composition of Example 3.3 | 3 h $CO_2$ | 5.7 | 9.6 | 85.1 | 6.9 |
| 3.17 | Composition of Example 3.3 | 24 h $CO_2$ | 5.6 | 4.9 | 77.5 | 19.7 |
| 3.18 | Composition of Example 3.3 | 48 h $CO_2$ | 5.8 | 8.2 | 68.2 | 27.4 |
| 3.19 | Composition of Example 3.3 | 72 h $CO_2$ | 5.7 | 9.4 | 65.9 | 28.3 |
| 3.20 | Composition of Example 3.3 | 0.5 h air | 5.8 | 9.2 | 89.0 | 4.5 |
| 3.21 | Composition of Example 3.3 | 1 h air | 5.7 | 12.4 | 85.9 | 4.4 |
| 3.22 | Composition of Example 3.3 | 2 h air | 5.9 | 18.0 | 80.5 | 4.3 |
| 3.23 | Composition of Example 3.3 | 3 h air | 5.6 | 20.7 | 77.9 | 4.3 |
| 3.24 | Composition of Example 3.3 | 24 h air | 5.8 | 24.3 | 69.3 | 9.1 |
| 3.25 | Composition of Example 3.3 | 48 h air | 5.7 | 25.4 | 64.3 | 13.9 |
| 3.26 | Composition of Example 3.3 | 72 h air | 5.7 | 26.8 | 62.2 | 14.3 |

As can be seen from the results in Table 1 the compositions of the invention, wherein the oxygen carrier is charged with CO, not only can be stored for a long time without forming methemoglobin, but further are able to replace the bound CO by $O_2$ when it is offered to the charged oxygen carrier. If exposed to 100% $O_2$ (examples 3.6 to 3.12) the $O_2$ saturation of the hemoglobin increases very fast.

If the composition is exposed to $CO_2$, representing the situation inside of mammalian pathway-active tissue, an increased amount of methemoglobin is formed (examples 3.13 to 3.19).

As can be seen the content of $O_2$ in freshly prepared samples (Example 3.2) is around 27%. Said content remains stable during storage (see Examples 3.4 and 3.5), however, the methemoglobin content increases undesirably. Considering Examples 3.20 to 3.26 the surprising result is that within 3 hours the CO comprising composition exposed to air is charged with 20.7% oxygen, but still has a very low methemoglobin content. When a body surface is treated, the composition is applied to the (cleaned) surface and remains in contact with air.

These results show that a composition according to the invention comprises a stabilized oxygen carrier which after several months of storing provides high oxygen transport when it is in contact with air.

Example 4

In total 100 persons suffering from a Herpes zoster infection (Shingles) and reporting about painful feelings where divided into two groups of 50 patients each, which in view of severity of the disease, age and sex of the patients and further conditions were comparable.

All the patients of both groups were treated by obtaining a classic standard Shingles treatment therapy (oral application of an antiviral medicament). In Group 1 the patients additionally were treated by spraying a sterile saline solution as a thin film to the body areas affected by Shingles. In Group 2, however, the patients were treated by spraying a thin film of a composition as prepared according to Example 1 to the body areas affected by Shingle blisters ("Standard of Care" plus Granulox® application at each treatment of shingles). Spray applications were carried out twice a week by topical application of the hemoglobin spray Granulox® (Sastomed, Georgsmarienhütte, Germany), a composition according to Example 1.

All the patients were treated until the visible syndromes were healed and the unpleasant feeling (itching, stinging, pain etc.) was overcome.

Data were collected twice weekly for four weeks then weekly until the patient was discharged (healed/Pain free) or at 12 weeks stage where the study data collection and patient follow up will cease.

Pain reduction over time (Visual analogue score 0=no pain, 10 =maximal pain) and time to heal was evaluated by questionnaires with scoring tools.

Group 1: "Saline group": 50 patients
Male: 29
Female: 21
Age range: 16 to 89 years
Pyrexia on day 0: 23 patients
Rash: 9
Blister: 35
Erythema: 3
Other: 3 (pain only)
Oral Aciclovir medicaments as standard: 49
(1 patient had allergy)
Self care with skin wash saline: 50
Pain range in days: 15 to 59
Healing days: 5 to 43
Group 2: "Granulox® group": 50 patients
Male: 26
Female 24
Age range: 17 to 90 years
Pyrexia on day 0: 26 patients
Rash: 3
Blister: 36
Erythema: 5
Other: 6 (pain only)
Oral acyclovir application: 50

Self care with Granulox®: 50
Pain range in days: 9 to 30
Healing days: 5 to 18

As can be seen in the above results the time period of painful feelings elicited by the underlying disease noticeably decreases when the patients were treated with the hemoglobin spray Granulox® instead of saline. Also the visible symptoms (blisters, red dots) are much faster reduced when Granulox® was applied to the affected body areas. Thus, due to the positive effect of the hemoglobin spray the healing time was impressively shorter.

The invention claimed is:

1. A method for treating pain, itching, stinging, a burning feeling, numbness or swelling of skin of a patient due to a disorder or disease affecting the somatosensory nervous system, the method comprising applying a composition to skin of the patient, the composition comprising
   (a) an oxygen carrier having at least 40% of oxygen-binding sites charged with a non-$O_2$ ligand, and
   (b) at least one further ingredient, selected from electrolyte(s) preservative(s), stabilizer(s), anti-flocculant(s), anticoagulant(s), pH buffering agent(s), solvent(s), antioxidant(s), film-forming agent(s), ointment ingredients, oils, greases or fats, or crosslinking agent(s).

2. The method according to claim 1, wherein the composition is an aqueous or organic solution, a lotion, a cream, a gel, an ointment or a powder, or said composition is comprised in a plaster, bandage or dressing.

3. The method according to claim 1, wherein the composition comprises:
   (i) between about 40% to about 90% of the oxygen carrier provided in a form wherein the oxygen-binding sites are charged with a non-$O_2$ ligand,
   (ii) the oxygen carrier is a naturally occurring hemoglobin or myoglobin of human or animal origin, or is artificially treated, crosslinked or modified hemoglobin or myoglobin of human or animal origin; and
   (iii) the composition is provided in sterilized form.

4. The method according to claim 1, wherein the pain, itching, stinging, burning, numbness or swelling of a patient due to a disorder or disease occurs at body sites or body areas showing blebs, blisters, pimples, rash, red patches, or wheals.

5. The method according to claim 1, wherein the composition is provided in a packaging means comprising a container, a tube, a can, an aerosol can, airless dispenser, airless pump dispenser, airless tube, a spraying container or spraying flask, as far as such devices work without sucking back air after an application use, a one-unit-package, an ampulla, a pouch, sachet, package or blow-formed container.

6. A method for preparing a composition for use according to claim 1, comprising:
   (i) charging the oxygen carrier with the non-$O_2$ ligand during or after isolation from its natural environment,
   (ii) adding at least one further ingredient (b);
   (iii) sterilizing the composition by one or more of heating, filtration, centrifugation, addition of preservatives, vapour application, gas application or UV-application or any combination thereof; and
   (iv) packaging the composition.

7. The method of claim 6, wherein the oxygen carrier compound is isolated and purified from whole blood from a human, animal, or mammal.

8. The method according to claim 1, wherein the oxygen carrier is a naturally occurring hemoglobin or myoglobin of human or animal origin.

9. The method according to claim 1, wherein the non-$O_2$ ligand is selected from carbon monoxide or nitrogen monoxide.

10. The method according to claim 1, wherein the disorder or disease is caused by a virus.

11. The method according to claim 10, wherein the disorder or disease is caused by a Herpes virus, a Herpes Zoster virus, a Herpes simplex virus, shingles, chickenpox, or lip blisters.

12. The method according to claim 1, wherein the composition is provided in the form of a lotion, cream, or ointment and further comprises a cosmetically-acceptable oil, wax, grease, or fat commonly used in cremes, lotions, emulsions or ointments.

* * * * *